United States Patent
Treat et al.

[11] Patent Number: 5,595,565
[45] Date of Patent: Jan. 21, 1997

[54] SELF-PROPELLED ENDOSCOPE USING PRESSURE DRIVEN LINEAR ACTUATORS

[75] Inventors: Michael R. Treat, New York, N.Y.; William S. Trimmer, Belle Meade, N.J.

[73] Assignee: The Trustees of Columbia University in the City of New York, New York, N.Y.

[21] Appl. No.: 268,641

[22] Filed: Jun. 30, 1994

[51] Int. Cl.⁶ ............................. A61B 1/00; G01D 21/00
[52] U.S. Cl. .................... 600/114; 600/101; 600/122; 73/866.5
[58] Field of Search ................ 128/4–10; 73/865.8, 73/866.5; 901/1; 604/95; 165/11.2; 600/101, 114, 122

[56] References Cited

U.S. PATENT DOCUMENTS

| | | |
|---|---|---|
| 2,855,934 | 10/1958 | Daughaday . |
| 3,665,928 | 5/1972 | Del Guercio ............... 604/95 |
| 3,895,637 | 7/1975 | Choy . |
| 4,207,872 | 6/1980 | Meiri et al. .................. 128/4 |
| 4,593,699 | 6/1986 | Poncy et al. . |
| 4,646,722 | 3/1987 | Silverstein et al. . |
| 4,769,006 | 9/1988 | Papantonakos . |
| 4,809,678 | 3/1989 | Klein . |
| 4,907,395 | 3/1990 | Opie et al. . |
| 4,934,786 | 6/1990 | Krauter . |
| 5,088,178 | 2/1992 | Stolk . |
| 5,090,259 | 2/1992 | Shishido et al. ............ 73/866.5 |
| 5,159,919 | 11/1992 | Chikama . |
| 5,337,732 | 8/1994 | Grundfest et al. ............ 128/4 |

*Primary Examiner*—Richard J. Apley
*Assistant Examiner*—John P. Leubecker
*Attorney, Agent, or Firm*—John P. White

[57] ABSTRACT

An articulated endoscope for performing endoscopic procedures in a tubular organ of a patient is provided, comprising a chassis, a plurality of pressure driven linear actuators mounted, by proximal ends, in oppositely facing pairs to the chassis, control means mounted to the chassis for storing a predetermined pressure distribution sequence therein and for outputting the predetermined sequence in response to a directional input from a user, means for receiving and distributing pressure to the plurality of pressure driven linear actuators in the predetermined pressure distribution sequence in response to control signals from the control means, the means for receiving and distributing being mounted to the chassis, and a tube delivering pressure to the means for receiving and distributing pressure, whereby self-propelled motive force is produced by pushing against interior surfaces of the tubular organ with distal ends of the plurality of pressure driven linear actuators as pressure is applied to the plurality of pressure driven linear actuators in the predetermined pressure distribution sequence.

44 Claims, 3 Drawing Sheets

SELF-PROPELLED ENDOSCOPE USING PRESSURE DRIVEN LINEAR ACTUATORS

BACKGROUND OF THE INVENTION

The present invention relates to a self-propelled endoscope apparatus for performing endoscopic procedures in which many of the hazards posed by conventional endoscopes are eliminated.

Within this application several publications are referenced by arabic numerals within parentheses. Full citations for these and other references may be found at the end of the specification immediately preceding the claims. The disclosures of all of these publications in their entireties are hereby incorporated by reference into this application in order to more fully describe the state of the art to which this invention pertains.

One of the major applications of gastrointestinal endoscopy is the detection of pre-malignant and malignant lesions of the gastrointestinal tract. There are approximately 250,000 new cases of colon cancer diagnosed in the United States every year. Approximately 50,000 of these people die of colon cancer every year. Colon cancer represents the number one killing cancer affecting both sexes nearly equally (breast cancer is much more common in women than in men). Not only in the United States, but in Western societies in general, colon cancer is a major health problem (1).

Despite the lethality of colon cancer, there exists an opportunity for its prevention by detecting and removing the precursor of the actual cancer. This precursor lesion is the polyp. This is a small (generally less than 1 cm diameter) growth on the lining of the bowel. It represents an area of the lining of the bowel which has undergone neoplastic transformation—i.e. clones of the cells which have undergone a genetic change enabling them to escape the regulatory systems controlling normal cell growth. While a polyp is neoplastic, it is still benign, since it is not capable of invading other structures or of metastasizing to other locations.

Endoscopic technology permits the detection and removal of polyps from the gastrointestinal tract without resorting to major invasive surgery. When polyps are endoscopically removed, they generally do not recur. However, if polyps are not removed, some of them will undergo malignant transformation and become cancers. A cancer is capable of infiltrating its cells into normal tissues, and is also capable of metastasizing. Unlike polyps, a cancer will recur unless a fairly radical operation is done. Unfortunately, the overall cure rate for colon cancers is less than 50% even if extensive surgery is done.

Theoretically, if one could detect and remove all colon polyps, the incidence of colon cancer would be very low (there are probably some cancers that arise de novo, without a preceding benign polyp precursor) (2). Flexible endoscopes (e.g. colonoscopes) make this possible.

Conventional endoscopes are constructed as follows: there is a long flexible shaft, with a diameter suitable to the organ for which it is intended. A flexible colonoscope is about 14 mm in diameter and 180 cm in length. The shaft is encased with a metallic double helical spiral that resists torsional deformation while permitting axial flexibility. The distal 8 cm of the endoscope, the bending section, is a stacked series of universal joints. Wires operated by controls at the proximal end of the endoscope cause the bending section to bend in whatever direction is desired. The shaft also contains fiberoptic bundles to bring light to the scene at the tip of the endoscope. A video chip with appropriate optics and video electronics is mounted at the tip of the endoscope and the image is conveyed by wires back to the operator. The shaft of the endoscope also incorporates small tubes to bring air and water into the field. The air is used to open up the bowel to obtain a clear view. The water is used to clean the endoscope's optics. The shaft also contains a channel to pass instruments such as biopsy forceps or snares to remove polyps.

Essentially, the operator of the endoscope pushes it into the bowel. The scope is of necessity flexible so that it can fit around the curvatures of the bowel. The bowel itself is not only curved but also is capable of stretching or being looped into curves which are exaggerations of the normal anatomic position. Therefore, as the endoscope is pushed into the bowel, it stretches the bowel. When the bowel is forced into these stretched loops by the insertion of the endoscope, the patient is made uncomfortable. If the doctor does not recognize that the bowel is being unduly stretched, the bowel wall will tear and a perforation occurs, requiring an emergency operation to repair (3). A skilled operator of the endoscope can avoid excessive stretching or looping, but even a skilled operator cannot avoid causing some discomfort to the patient and very occasionally even serious harmful effects. Manipulating the shaft of the endoscope so that excessive looping does not occur is a blind process. The operator is aware by direct endoscopic vision of what lies ahead of the endoscope, but he is only indirectly aware of how the shaft is interacting with the bowel to form loops. Thus, even a skilled operator may not be aware of the formation of an excessive loop and a serious complication may ensue (4).

Additionally, a conventional endoscope cannot be sterilized in the same way as a simple stainless steel surgical instrument. This lack of absolute sterilizability results from the conventional endoscope's complex hybrid construction of metallic parts, plastic parts, electronics and optics which would be destroyed by the high temperatures used in steam autoclaves. These instruments can be sterilized by use of an ethylene oxide gas process ("gas sterilization"), but this procedure requires approximately six to eight hours. Since endoscopes are expensive, it is not practical to have enough endoscopes in reserve to do all the procedures that one might do in one day. Therefore, what is conventionally done is "cold soaking", which refers to the use of a bactericidal/viricidal liquid such as glutaraldehyde to achieve a high degree of disinfection. This process takes about a half hour to perform, which is compatible with the turn-over requirements of an endoscopy unit. However, a high level of disinfection is not the same as absolute sterilization by autoclave. In addition, the actual ability of the glutaraldehyde to achieve high disinfection is dependent on diligent pre-cleaning of mucus and other substances from the numerous channels and crevices which exist in the endoscope. If this tenacious debris is not removed, the glutaraldehyde will not be able to penetrate to achieve killing of micro-organisms (5,6).

SUMMARY OF THE INVENTION

It is an object of the present invention to provide an arrangement for performing endoscopic procedures in which many of the hazards posed by conventional endoscopes are eliminated.

It is a further object of the present invention to provide an arrangement in which endoscopic procedures may be safely and comfortably carried out in various tubular organs of a patient.

It is yet a further object of the present invention to provide an arrangement in which endoscopic procedures may be carried out without looping the gastrointestinal tract of a patient.

It is yet a further object of the present invention to provide an arrangement in which endoscopic procedures may be carried out without puncturing the wall of a patent's gastrointestinal tract.

It is yet a further object of the present invention to provide an arrangement in which endoscopic procedures may be carried out that would be difficult to perform with a conventional endoscope because of the finite bending radius imposed by the shaft.

It is yet a further object of the present invention to provide an arrangement in which endoscopic procedures may be carried out free from the risk of cross-contamination between patients.

It is yet a further object of the present invention to provide an arrangement in which an articulated endoscope includes reusable components encased in an inexpensive disposable outer sheath, thus allowing the patient to benefit from advanced technology which itself is too costly to be disposable, while maintaining the advantage of freedom from risk of cross contamination from another patient.

According to one aspect of the present invention, an articulated endoscope for performing endoscopic procedures in a tubular organ of a patient is provided, comprising a chassis, a plurality of pressure driven linear actuators mounted at their proximal ends, in oppositely facing pairs on the chassis, control means mounted on the chassis for storing a predetermined pressure distribution sequence therein and for outputting the predetermined sequence in response to a directional input from a user, means for receiving and distributing pressure to the plurality of pressure driven linear actuators in the predetermined pressure distribution sequence in response to control signals from the control means, the means for receiving and distributing being mounted on the chassis, and a tube delivering pressure to the means for receiving and distributing pressure, whereby self-propelled motive force is produced by pushing against interior surfaces of the tubular organ with distal ends of the plurality of pressure driven linear actuators as pressure is applied to the plurality of pressure driven linear actuators in the predetermined pressure distribution sequence.

The present invention also provides an articulated endoscope for performing endoscopic procedures in a tubular organ of a patient comprising a chassis, a plurality of pressure driven linear actuators, the plurality of pressure driven linear actuators being pivotally mounted on the chassis at their proximal ends, in oppositely facing pairs, pressure driven pivoting means for pivoting respective ones of the oppositely facing pressure driven linear actuators, a plurality of rods mounted at distal ends of respective ones of the plurality of pressure driven linear actuators, control means mounted on the chassis for storing a predetermined pressure distribution sequence therein and for outputting the predetermined sequence in response to a directional input from a user, means for receiving and distributing pressure to the plurality of pressure driven linear actuators and the pressure driven pivoting means in the predetermined pressure distribution sequence, and a tail with at least one tube for delivering pressure to the means for receiving and distributing, the means for receiving and distributing being mounted on the chassis and self-propelled motive force being produced by pushing against interior surfaces of the tubular organ with distal ends of the plurality of rods as pressure is applied to the plurality of pressure driven linear actuators and the pressure driven pivoting means in the predetermined pressure distribution sequence.

The present invention also provides a self-propelling device for insertion and longitudinal movement within an elongated passage having a tubular wall, the device comprising a rigid chassis insertable in the elongated passage for carrying a payload for performing a procedure within the passage, a plurality of rigid legs carried by the chassis and movable relative thereto, each of the legs having a distal end, the legs projecting laterally from the chassis such that their distal ends are respectively disposed for engagement with spaced-apart portions of the tubular wall, means, carried by the chassis and connected to the legs, for actuating the legs to move for propelling the chassis along the passage, means carried by the chassis for controlling the actuating means to effect movement of the legs, and a thin elongated flexible tail extending from the chassis for transmitting motive power to the actuating means and control signals to the controlling means from a locality external to the passage when the chassis is inserted within the passage.

These and other advantages will become apparent from the detailed description accompanying the claims and attached drawing figures.

DETAILED DESCRIPTION OF THE PREFERRED EMBODIMENTS

Figure 1:
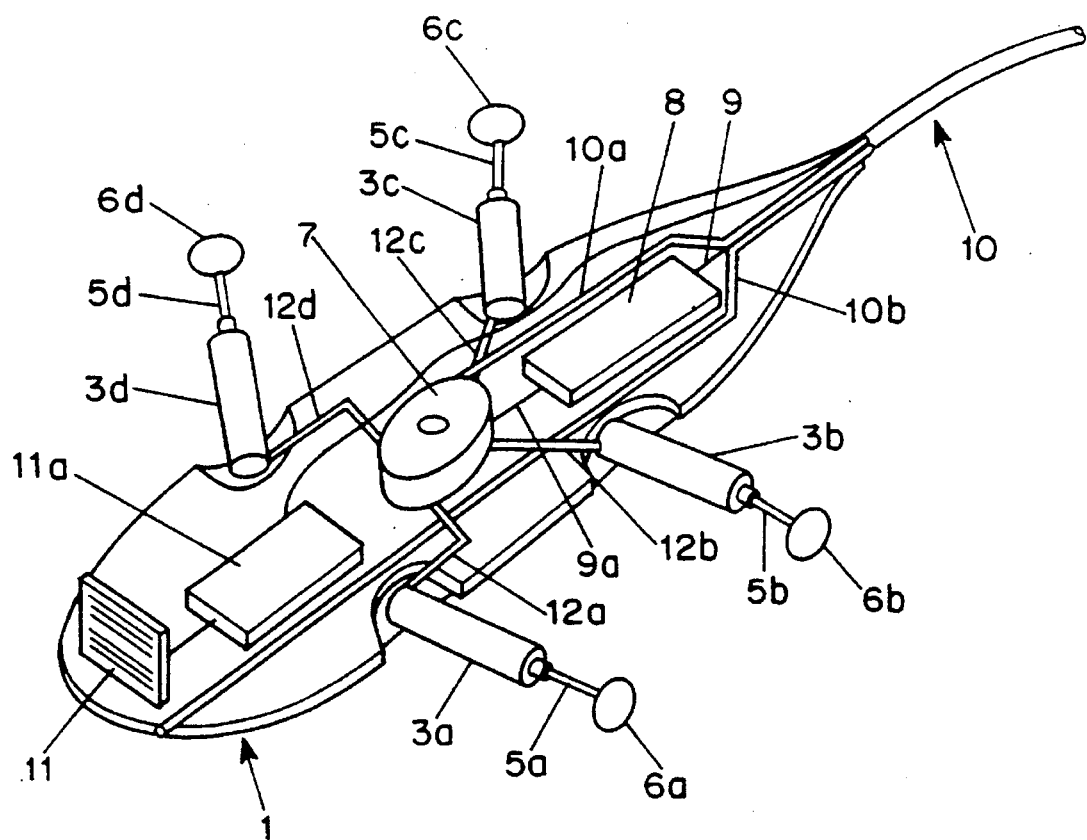
FIG. 1 is an articulated endoscope apparatus according to a first embodiment of the present invention.

According to one aspect of the present invention, an articulated endoscope for performing endoscopic procedures in a tubular organ of a patient is provided, comprising a chassis, a plurality of pressure driven linear actuators mounted, by proximal ends, in oppositely facing pairs to the chassis, control means mounted to the chassis for storing a predetermined pressure distribution sequence therein and for outputting the predetermined sequence in response to a directional input from a user, means for receiving and distributing pressure to the plurality of pressure driven linear actuators in the predetermined pressure distribution sequence in response to control signals from the control means, the means for receiving and distributing being mounted to the chassis, and a tube delivering pressure to the means for receiving and distributing pressure, whereby self-propelled motive force is produced by pushing against interior surfaces of the tubular organ with distal ends of the plurality of pressure driven linear actuators as pressure is applied to the plurality of pressure driven linear actuators in the predetermined pressure distribution sequence.

According to another aspect of the present invention, the plurality of pressure driven linear actuators are pneumatically driven.

According to another aspect of the present invention, the plurality of pressure driven linear actuators are hydraulically driven.

According to another aspect of the present invention, the predetermined pressure distribution sequence causes the endoscope to move forward through the tubular organ.

According to another aspect of the present invention, a plurality of rods may be mounted to distal ends of respective ones of the plurality of pressure driven linear actuators.

According to another aspect of the present invention, a removable sheath may be mounted over the plurality of pressure driven linear actuators, the plurality of rods, the chassis, and the means for receiving and distributing pressure.

According to another aspect of the present invention, the means for receiving and distributing the pressure further comprises a valve.

According to another aspect of the present invention, the valve further comprises a shape metal alloy valve which employs shape metal alloys as pressure regulation means.

According to another aspect of the present invention, the control means responds to electronic signals transmitted by a user through electronic signal transmitting means connected to the control means.

According to another aspect of the present invention, the control means responds to light signals transmitted by a user through fiber-optic signal transmitting means connected to the control means.

The present invention also provides an articulated endoscope for performing endoscopic procedures in a tubular organ of a patient comprising a chassis, a plurality of pressure driven linear actuators, the plurality of pressure driven linear actuators being pivotally mounted, by proximal ends, in oppositely facing pairs to the chassis, pressure driven pivoting means for pivoting respective ones of the oppositely facing pressure driven linear actuators, a plurality of rods mounted to distal ends of respective ones of the plurality of pressure driven linear actuators, control means mounted to the chassis for storing a predetermined pressure distribution sequence therein and for outputting the predetermined sequence in response to a directional input from a user, means for receiving and distributing pressure to the plurality of pressure driven linear actuators and the pressure driven pivoting means in the predetermined pressure distribution sequence, and a tail with at least one tube for delivering pressure to the means for receiving and distributing, whereby the means for receiving and distributing is mounted to the chassis and self-propelled motive force is produced by pushing against interior surfaces of the tubular organ with distal ends of the plurality of rods as pressure is applied to the plurality of pressure driven linear actuators and the pressure driven pivoting means in the predetermined pressure distribution sequence.

According to another aspect of the present invention, the pressure driven pivoting means are pneumatically driven.

According to another aspect of the present invention, the pressure driven pivoting means are hydraulically driven.

According to another aspect of the present invention, the tail is removable.

According to another aspect of the present invention, the predetermined pressure distribution sequence causes the chassis to move backward through the tubular organ.

According to another aspect of the present invention, a removable sheath is provided for covering the chassis, the plurality of pressure driven linear actuators, the plurality of rods, the pressure driven pivoting means, the means for receiving and distributing, and the tail.

According to another aspect of the present invention, a plurality of load spreading members mounted on respective ones of the plurality of rods are provided to spread the force produced by the distal ends of the rods as they push against the interior surface of the tubular organ over a larger surface area, the plurality of load spreading members being covered by the removable sheath.

According to another aspect of the present invention, the plurality of load spreading members are beads.

According to another aspect of the present invention, the plurality of beads are compressible.

According to another aspect of the present invention, an imaging means mounted on the chassis is provided, the imaging means being covered by the removable sheath.

According to another aspect of the present invention, the removable sheath includes a transparent window in register with the imaging means.

According to another aspect of the present invention, the tail further comprises at least one tube for carrying fluid to the exterior of the sheath, whereby the fluid cleans the transparent window.

According to another aspect of the present invention, the tail further comprises at least one conduit terminating outside the sheath for guiding surgical instruments.

According to another aspect of the present invention, the pressure applied to the interior surface of the tubular organ by the load spreading members is less than the pressure necessary to puncture a gastrointestinal tract.

According to another aspect of the present invention, the pressure applied to the interior surface of the tubular organ by the load spreading members is less than the pressure necessary to puncture a urinary tract.

According to another aspect of the present invention, the pressure applied to the interior surface of the tubular organ by the load spreading members is less than the pressure necessary to puncture a member of the vascular system.

According to another aspect of the present invention, the imaging means further comprises a charge coupled device.

According to another aspect of the present invention, the imaging means further comprises a video driver.

Referring now to the drawings, FIG. 1 shows an articulated endoscope apparatus according to a first embodiment of the present invention. The apparatus is particularly suited for endoscopic procedures in the gastrointestinal tract, urinary tract, or vascular system. The preferred embodiment will be described with reference to the gastrointestinal tract, but this is by way of example and not by way of limitation.

The apparatus comprises a rigid chassis 1, supporting, by their proximal ends, a plurality of linear actuators 3a, 3b, 3c, and 3d arranged in oppositely facing pairs. The linear actuators may be pressure driven actuators, such as pneumatically or hydraulically driven actuators, for example. In this embodiment, the two pressure driven linear actuators comprising each pair are mounted at a fixed angular relationship to one another, each actuator extending outwardly and obliquely rearwardly from the chassis. Rigid leg members 5a, 5b, 5c, and 5d are mounted on distal ends of respective ones of the pneumatic linear actuators 3a, 3b, 3c, and 3d. The leg members may be, for example, metal or plastic rods. Load spreading members 6a, 6b, 6c, and 6d are mounted on distal ends of respective leg members 5a, 5b, 5c, 5d. The load spreading members may be in the form of pads or beads, and may be either rigid or compressible. Means for receiving and distributing pressure 7 to the plurality of linear actuators 3a, 3b, 3c, and 3d is mounted to chassis 1. The means for receiving and distributing pressure 7, which may (for example) be a pneumatic mini-value, receives pressure from a supply means (not shown) through tube 10a within tail 10 and distributes the pressure to respective ones of the linear actuators 3a, 3b, 3c, and 3d through tubes 12a, 12b, 12c, and 12d. Control electronics 8, also mounted on the chassis, has a predetermined pressure distribution sequence stored therein and the means for receiving and distributing pressure 7 distributes the pressure in the predetermined sequence in response to control signals carried by signal carrying means 9a (such as a wire or fiber-optic cable) from control electronics 8, which receives directional input from a user, such as a forward or backward command, and sends the predetermined sequence of control signals to the means for receiving and distributing pressure 7 in response to the directional input. The control means 8 receives directional input from a user via a signal transmitting means 9 within tail 10. The signal transmitting means 9 may be, for example, a wire or a fiber-optic cable imaging means 11 is mounted to chassis 1 and is connected by a wire or fiber-optic cable to video electronics 11a. Video electronics 11a are connected through a wire or fiber-optic cable running through tail 10 to an external video system (not shown). Tube 10b, within tail 10, carries air or water for cleaning purposes.

The operation of an articulated endoscope according to a first embodiment of the present invention is as follows. The chassis is inserted into a patient's gastrointestinal tract (not shown). The means for receiving and distributing pressure 7 receives pressure from the supply means (not shown) through tube 10a and distributes the pressure to the plurality of linear actuators 3a, 3b, 3c, and 3d in the predetermined sequence, under control of control electronics 8, which is receiving directional input from the user. The predetermined sequence could be, for example, the retraction of the forward legs coupled with extension of the rear legs followed by the extension of the forward legs coupled with retraction of the rear legs, thus propelling the chassis forward. After reaching a given site within the gastrointestinal tract, the chassis may be removed from the patient by retracting all of the legs and pulling the chassis out of the patient's body by the tail 10.

Figure 2:
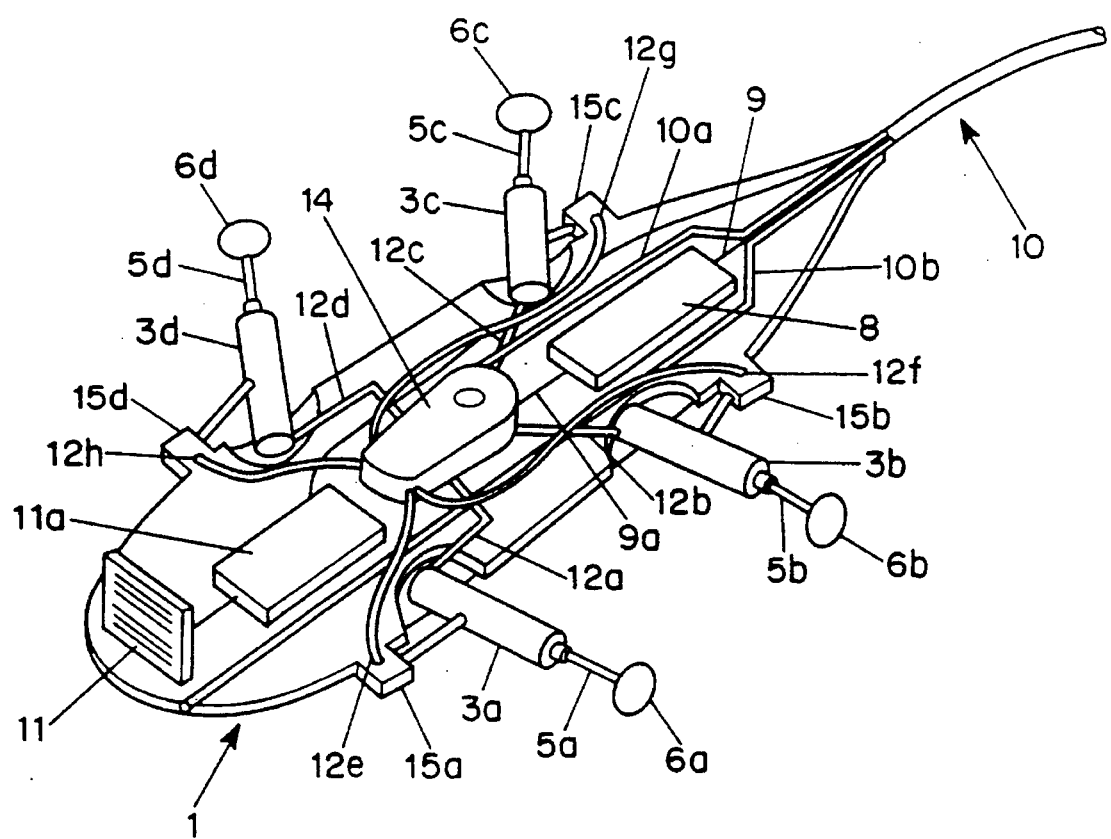
FIG. 2 is an articulated endoscope apparatus according to a second embodiment of the present invention.

Referring now to FIG. 2, wherein the same reference numerals of FIG. 1 are applied to the same parts and therefore do not require detailed description, an articulated endoscope apparatus according to a second embodiment of the present invention is shown. In this Fig., the plurality of linear actuators 3a, 3b, 3c, and 3d are pivotally mounted to the chassis 1 and are pivoted by pressure driven pivoting means 15a, 15b, 15c, and 15d, mounted to chassis 1 and respective ones of the plurality of linear actuators 3a, 3b, 3c, and 3d. As in the case of the first embodiment, the pressure driven linear actuators may be pneumatically or hydraulically driven, as may be the pressure driven pivoting means.

The operation of an articulated endoscope according to the second embodiment of the present invention is as follows. The chassis is inserted into a patient's gastrointestinal tract (not shown). A means for receiving and distributing pressure 14 receives pressure from the supply means (not shown) through tube 10a and distributes the pressure to the plurality of linear actuators 3a, 3b, 3c, and 3d and the pivoting means 15a, 15b, 15c, and 15d through tubes 12a, 12b, 12c, 12d, 12e, 12f, 12g, and 12h. Control electronics 8 has a predetermined pressure distribution sequence stored therein and the means for receiving and distributing pressure 14 distributes the pressure in the predetermined sequence in response to control signals from control electronics 8, which receives directional input from a user, such as a forward or backward command, and sends the predetermined sequence of control signals to the means for receiving and distributing pressure 14 in response to the directional input. The control means 8 receives directional input from a user via a signal transmitting means 9 within tail 10. The signal transmitting means may be, for example, a wire or a fiber-optic cable. Imaging means 11 is mounted to chassis 1 and is connected by a wire or fiber-optic cable to video electronics 11a. Video electronics 11a are connected through a wire or fiber-optic cable running through tail 10 to an external video system (not shown). For the purposes of this explanation, forward is taken to mean further into the patient and backward is take to mean out of the patient. The predetermined sequence could be, for example, the retraction of the legs 5a, 5b, 5c, and 5d coupled with forward pivoting of the linear actuators 3a, 3b, 3c, and 3d by respective pivoting means 15a, 15b, 15c, and 15d followed by the extension of legs 5a, 5b, 5c, and 5d and the backward pivoting of the linear actuators 3a, 3b, 3c, and 3d by respective pivoting means 15a, 15b, 15c, and 15d, thus propelling the chassis forward.

The direction of travel may also, of course, be reversed by reversing the above sequence. In this case, the plurality of linear actuators 3a, 3b, 3c, and 3d are first pivoted by respective pivoting means 15a, 15b, 15c, and 15d so that their distal ends face the forward end of the chassis. Then, the retraction of the legs 5a, 5b, 5c, and 5d coupled with backward pivoting of the linear actuators 3a, 3b, 3c, and 3d by pivoting means 15a, 15b, 15c, and 15d followed by the extension of legs 5a, 5b, 5c, and 5d and the forward pivoting of the pivoting means 15a, 15b, 15c, and 15d, propels the chassis backward. In addition, as in the first embodiment, the chassis may be removed from the patient by retracting all of the legs 5a, 5b, 5c, and 5d and pulling the chassis out of the patient's body by the tube 10.

Figure 3:
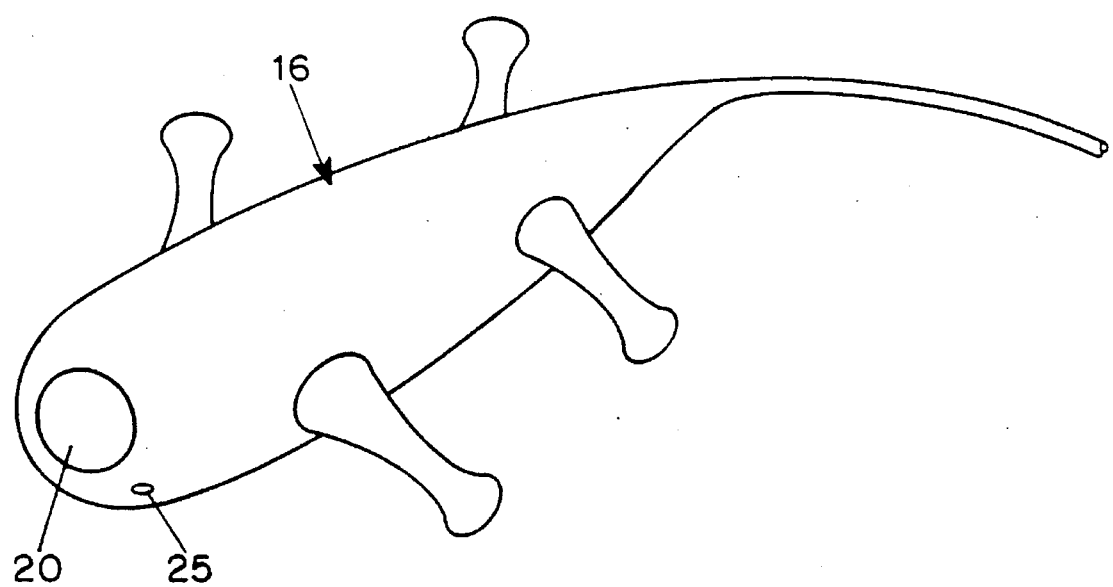
FIG. 3 is an articulated endoscope apparatus according to a first embodiment of the present invention that is covered by a removable sheath.

Referring now to FIG. 3, wherein the same reference numerals of FIG. 1 are applied to the same parts and therefore do not require detailed description, an articulated endoscope apparatus according to the first embodiment of the present invention is shown covered by a removable sheath. In this Figure, a sheath 16 is shown covering the chassis 1, the plurality of linear actuators 3a, 3b, 3c, and 3d, the leg members 5a, 5b, 5c, and 5d, the load spreading members 6a, 6b, 6c, and 6d, the means for receiving and distributing pneumatic pressure 7, the imaging means 11, and at least part of the tail 10. The sheath includes a transparent portion 20 in register with the imaging means so as to allow light to pass through the sheath onto the imaging means. A port 25 gives tube 10b access to the exterior of the sheath for expelling air or water or for extending surgical instruments such as snares therethrough. After removal from the patient, the sheath is discarded and a new one is installed over the chassis 1, the plurality of linear actuators 3a, 3b, 3c, and 3d, the leg members 5a, 5b, 5c, and 5d, the load spreading members 6a, 6b, 6c, and 6d, the means for receiving and distributing pressure 7, the imaging means 8, and at least part of the tube 10 in order to reduce the risk of cross-contamination between patients.

It must be noted that although the present invention is described by reference to particular embodiments thereof, many changes and modifications of the invention may become apparent to those skilled in the art without departing from the spirit and scope of the invention, which is only limited by the appended claims. Therefore, the embodiments shown and described are only illustrative, not restrictive.

REFERENCES

1. Fenoglio-Preiser, C. M., Lantz, P. E., Listrom, M. B., Davis, M, Rilke, F. O., *The Neoplastic Large Intestine,*

Gastrointestinal Pathology, An Atlas and Text, Raven Press, New York, N.Y. 1989.

2. Guillem, J. G., Forde, K. A., Treat, M. R., Neugut, A. I., O'Toole, K. M., Diamond, B. E., *Colonoscopic screening for neoplasms in asymptomatic first-degree relatives of colon cancer patients. A controlled, prospective study*, Dis Colon Rectum. 35(6):523–9, 1992.

3. *Complications of colonoscopy*, Colonoscopy (Eds. Hunt and Way, J. G.), 1989.

4. Gores, P. F., Simso, L. A., *Splenic injury during colonoscopy*, Arch Surg 124:1342, 1989.

5. Porter, J. V., Connell, P. A., Crow, S, Reichert, M., *Endoscope disinfection and sterilization: not a black-and-white issue*, Todays OR Nurse 15(3):27–30, 1993.

6. Kaczmarek, R. G., Moore, R. M., Jr., McCrohan, J., Goldmann, D. A., Reynolds, C., Caquelin, C., Israel, E., *Multi-state investigation of the actual disinfection/sterilization of endoscopies in health care facilities*, Am J Med 92(3)L257–261, 1992.

What is claimed is:

1. An articulated endoscope for performing endoscopic procedures in a tubular organ of a patient comprising:

a single chassis;

four pressure driven linear actuators mounted, by proximal ends, in two oppositely facing pairs to the chassis, whereby said proximal ends of said four pressure driven linear actuators are mounted to respective mounting points on the single chassis and the respective mounting points do not move relative to one another;

control means mounted to the chassis for storing a predetermined pressure distribution sequence therein and for outputting the predetermined sequence in response to a directional input from a user;

means for receiving and distributing pressure to the four pressure driven linear actuators in the predetermined pressure distribution sequence in response to control signals from the control means, the means for receiving and distributing being mounted to the chassis; and a tube delivering pressure to the means for receiving and distributing pressure, whereby self propelled motive force is produced by pushing against interior surfaces of the tubular organ with distal ends of the four pressure driven linear actuators as pressure is applied to the four pressure driven linear actuators in the predetermined pressure distribution sequence.

2. The articulated endoscope of claim 1, wherein the four pressure driven linear actuators are pneumatically driven.

3. The articulated endoscope of claim 1, wherein the four pressure driven linear actuators are hydraulically driven.

4. The articulated endoscope of claim 1, wherein the control means stores a predetermined pressure distribution sequence which causes the endoscope to move forward through the tubular organ.

5. The articulated endoscope of claim 1, further comprising four rods mounted to distal ends of respective ones of the four pressure driven linear actuators.

6. The articulated endoscope of claim 5, further comprising a removable sheath mounted over the four pressure driven linear actuators, the four rods, the chassis, and the means for receiving and distributing pressure.

7. The articulated endoscope of claim 6, wherein the means for receiving and distributing the pressure further comprises a valve.

8. The articulated endoscope of claim 7, wherein the valve further comprises a shape metal alloy valve which employs shape metal alloys as pressure regulation means.

9. The articulated endoscope of claim 7, wherein the control means responds to electronic signals transmitted by a user through electronic signal transmitting means connected to the control means.

10. The articulated endoscope of claim 7, wherein the control means responds to light signals transmitted by a user through fiber-optic signal transmitting means connected to the control means.

11. An articulated endoscope for performing endoscopic procedures in a tubular organ of a patient comprising:

a chassis;

a plurality of pressure driven linear actuators, the plurality of pressure driven linear actuators being pivotally mounted, by proximal ends, in oppositely facing pairs to the chassis;

pressure driven pivoting means for pivoting respective ones of the oppositely facing pressure driven linear actuators;

a plurality of rods mounted to distal ends of respective ones of the plurality of pressure driven linear actuators;

control means mounted to the chassis for storing a predetermined pressure distribution sequence therein and for outputting the predetermined sequence in response to a directional input from a user;

means for receiving and distributing pressure to the plurality of pressure driven linear actuators and the pressure driven pivoting means in the predetermined pressure distribution sequence; and a tail with at least one cube for delivering pressure to the means for receiving and distributing;

whereby the means for receiving and distributing is mounted to the chassis and self-propelled motive force is produced by pushing against interior surfaces of the tubular organ with distal ends of the plurality of rods as pressure is applied to the plurality of pressure driven linear actuators and the pressure driven pivoting means in the predetermined pressure distribution sequence.

12. The articulated endoscope of claim 11, wherein the plurality of pressure driven linear actuators and pressure driven pivoting means are pneumatically driven.

13. The articulated endoscope of claim 11, wherein the plurality of pressure driven linear actuators and pressure driven pivoting means are hydraulically driven.

14. The articulated endoscope of claim 11, wherein the control meads stores a predetermined pressure distribution sequence which causes the chassis to move forward through the tubular organ.

15. The articulated endoscope of claim 11, wherein the control means stores a predetermined pressure distribution sequence which causes the chassis to move backward through the tubular organ.

16. The articulated endoscope of claim 11, wherein the tail is removable.

17. The articulated endoscope or claim 16, further comprising a removable sheath for covering the chassis, the plurality of pressure driven linear actuators, the plurality of rods, the pressure driven pivoting means, the means for receiving and distributing, and the tail.

18. The articulated endoscope of claim 17, further comprising a plurality of load spreading members mounted on respective ones of the plurality of rods to spread the force produced by the distal ends of the rods as they push against the interior surface of the tubular organ over a larger surface area, the plurality of load spreading members being covered by the removable sheath.

19. The articulated endoscope of claim 18, wherein the plurality of load spreading members are beads.

20. The articulated endoscope of claim 19, wherein the plurality of beads are compressible.

21. The articulated endoscope of claim 18, further comprising an imaging means mounted on the chassis, the imaging means being covered by the removable sheath.

22. The articulated endoscope or claim 21, wherein the removable sheath includes a transparent window in register with the imaging means.

23. The articulated endoscope of claim 22, wherein the tail further comprises at least one tube for carrying fluid to the exterior of the sheath, whereby the fluid cleans the transparent window.

24. The articulated endoscope of claim 23, wherein the tail further comprises at least one conduit terminating outside the sheath for guiding surgical instruments.

25. The articulated endoscope of claim 21, wherein the imaging means further comprises a charge coupled device.

26. The articulated endoscope of claim 21, wherein the imaging means further comprises a video driver.

27. The articulated endoscope of claim 18, wherein the control means stores a predetermined pressure distribution sequence which causes the plurality of pressure driven liner actuators to apply, to the interior surface of the tubular organ, through the load spreading members, a pressure which is less than the pressure necessary to puncture a gastrointestinal tract.

28. The articulated endoscope of claim 18, wherein the control means stores a predetermined pressure distribution sequence which causes the plurality of pressure driven linear actuators to apply, to the interior surface of the tubular organ, through the load spreading members, a pressure which is less than the pressure necessary to puncture a urinary tract.

29. The articulated endoscope of claim 18, wherein the control means stores a predetermined pressure distribution sequence which causes the plurality of pressure driven linear actuators to apply, to the interior surface of the tubular organ, through the load spreading members, a pressure which is less than the pressure necessary to puncture a member of the vascular system.

30. The articulated endoscope of claim 11, wherein the means for receiving and distributing the pressure further comprises a valve.

31. The articulated endoscope of claim 30, wherein the control means responds to electronic signals transmitted by a user through electronic signal transmitting means within the tail.

32. The articulated endoscope of claim 30, wherein the control means responds to light signals transmitted by a user through fiber-optic transmitting means within the tail.

33. The articulated endoscope of claim 30, wherein the valve further comprises a shape metal alloy valve which employs shape metal alloys as pressure regulation means.

34. A self propelling device for insertion and longitudinal movement within an elongated passage having a tubular wall, said device comprising:

a single rigid chassis insertable in the elongated passage for carrying a payload for performing a procedure within the passage;

four rigid legs carried by the chassis and movable relative thereto, each of said four legs having a distal end, said legs projecting laterally from said chassis such that their distal ends are respectively disposed for engagement with spaced apart portions of the tubular wall, and whereby respective proximal ends of said four rigid legs are mounted to respective mounting points on the single chassis and the respective mounting points do not move relative to one another;

means, carried by the chassis and connected to the four legs, for actuating each of the four legs to move for propelling the chassis along the passage;

means carried by the chassis for controlling the actuating means to effect movement of said four legs; and a thin elongated flexible tail extending from said chassis for transmitting motive power to said actuating means and control signals to said controlling means from a locality external to the passage when said chassis is inserted within the passage.

35. A device as defined in claim 34, wherein each of said four legs is mounted to be moved longitudinally by extension and retraction with respect to said chassis.

36. A device as defined in claim 34, wherein each of said four legs is mounted to be moved angularly with respect to said chassis.

37. A device as defined in claim 34, wherein said actuating means comprises a plurality of actuators, one for each of said four legs, each of said actuators being connected to one of said four legs and operable by fluid pressure to move the leg to which it is connected; wherein said controlling means comprises a fluid pressure distributor for controllably transmitting fluid pressure to said actuators in response to control signals; and wherein said tail includes a conduit for transmitting fluid pressure to said distributor.

38. A device as defined in claim 37, wherein said fluid pressure is gas pressure and said actuators are pneumatic actuators.

39. A device as defined in claim 34, wherein said distal ends of said four legs are enlarged and smooth surfaced terminal portions of said four legs for distributing pressure, exerted by said four legs, over extended surface areas of said wall.

40. A device as defined in claim 34, further including disposable flexible sheath means enclosing and shielding from contamination the chassis, legs, actuating means, controlling means, and tail, said sheath means being adapted to enclose and shield a payload from contamination when a payload is being carried by said device.

41. A device as defined in claim 34, further including a payload for performing a viewing procedure within the passage, said payload comprising viewing means carried by said chassis for obtaining visual image information, said tail including means for transmitting the visual image information to the exterior of the passage.

42. A device as defined in claim 34, wherein said four legs are arranged on said chassis in two pairs such that the distal ends of the legs of each pair are respectively disposed for engagement with opposite portions of the wall.

43. A device as defined in claim 34, dimensioned for insertion in a human intestinal tract.

44. A self propelling endoscopic device for insertion and longitudinal movement within a portion of a human intestinal tract having a wall, said device comprising:

a single rigid chassis insertable in the tract;

four rigid legs arranged in sets of two pairs carried by the chassis and movable relative thereto, each of said legs having an enlarged distal end, the legs of each pair projecting generally laterally from said chassis such that their distal ends are respectively disposed for engagement with opposite portions of the wall, and whereby respective proximal ends of said two pairs of rigid legs are mounted to respective mounting points on the single chassis and the respective mounting points do not move relative to one another;

a plurality of actuators, one for each leg, carried by the chassis, for actuating the legs to move relative to the chassis for propelling the chassis along the tract when the chassis is inserted in the tract and the leg distal ends engage the wall, each of said actuators being connected to one of said four legs and operable by fluid pressure to move the leg to which it is connected;

a fluid pressure distributor carried by the chassis for controllably transmitting fluid pressure to said actuators, to effect movement of said four legs, in response to control signals;

a thin elongated flexible tail extending from said chassis for transmitting fluid pressure and control signals to said distributor from a locality external to the tract when said chassis is inserted within the passage;

viewing means carried by said chassis for obtaining visual image information, said tail including means for transmitting the visual image information to the exterior of the tract; and disposable flexible sheath means enclosing said chassis, said four legs, said actuating means, said controlling means and said tail, for shielding the chassis, legs, actuating means and tail from contamination.

* * * * *